United States Patent
Yang

(10) Patent No.: US 7,029,915 B2
(45) Date of Patent: Apr. 18, 2006

(54) METHOD FOR DIFFERENTIATING RAT HEPATIC STEM CELLS TO INSULIN-PRODUCING CELLS

(75) Inventor: Lijun Yang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 171 days.

(21) Appl. No.: 10/373,124

(22) Filed: Feb. 24, 2003

(65) Prior Publication Data

US 2003/0223974 A1  Dec. 4, 2003

Related U.S. Application Data

(60) Provisional application No. 60/358,864, filed on Feb. 22, 2002.

(51) Int. Cl.
*C12N 5/02* (2006.01)
*C12N 5/00* (2006.01)
*C12N 5/06* (2006.01)

(52) U.S. Cl. .................. 435/377; 435/352; 435/353; 435/404; 435/405

(58) Field of Classification Search .............. 424/93.7; 435/325, 370, 377, 404
See application file for complete search history.

(56) References Cited

U.S. PATENT DOCUMENTS

| 5,834,308 A | 11/1998 | Peck et al. |
| 6,001,647 A | 12/1999 | Peck et al. |
| 2002/0182728 A1 | 12/2002 | Ramiya et al. |
| 2003/0031657 A1 | 2/2003 | Habener et al. |
| 2003/0138951 A1* | 7/2003 | Yin .......................... 435/370 |

OTHER PUBLICATIONS

Deutsch G et al. 2001. A bipotential precursor population for pancreas and liver within the embryonic endoderm. Development 128:871-881.*
Cambrex, Inc. product catalog for RPMI 1640 and DMEM culture media, and media formulation information for both. 6 pages. Website accessed May 4, 2005.*
Lester LB et al. 2004. Directed differentiation of rhesus monkey ES cells into pancreatic cell phenotypes. Reprod Biol Endocrinol 2: 42. 5 pages.*
Vogel, G., "Same Results, Different Interpretations," Stem Cell Research, 299: 324, 2003.
Horb et al., "Experimental Conversion of Liver to Pancreas", Current Biology, 13: 105-115, 2003.
Yang et al., "In vitro trans-differentiation of adult hepatic stem cells into pancreatic endocrine hormone-producing cells," PNAS Early Edition, 99: 1-6, 2002.

* cited by examiner

Primary Examiner—Sandra E. Saucier
Assistant Examiner—Lora E Barnhart
(74) Attorney, Agent, or Firm—Akerman Senterfitt

(57) ABSTRACT

Highly purified hepatic stem cells are trans-differentiated into pancreatic endocrine hormone-producing cells by culturing them in vitro in a medium containing high levels of glucose. These trans-differentiated cells express insulin, glucagon, and pancreatic polypeptide, but not hepatocyte protein Hep-par. When stimulated with glucose, these cells synthesize and secrete insulin, a response enhanced by nicotinamide. Transplantation of these trans-differentiated cells into a hyperglycemic animal normalizes blood sugar levels in the animal.

14 Claims, 3 Drawing Sheets

METHOD FOR DIFFERENTIATING RAT HEPATIC STEM CELLS TO INSULIN-PRODUCING CELLS

CROSS REFERENCE TO RELATED APPLICATIONS

This application claims priority from U.S. provisional patent application Ser. No. 60/358,864, filed Feb. 22, 2002.

STATEMENT AS TO FEDERALLY SPONSORED RESEARCH

This invention was made with United States government support under grant numbers DK58614 and DK60015 awarded by the National Institutes of Health. The United States government may have certain rights in the invention.

FIELD OF THE INVENTION

The invention relates generally to the fields of developmental biology, stem cells, endocrinology, and medicine. More particularly, the invention relates to pancreatic endocrine hormone-producing cells made from hepatic stem cells, and methods of making and using such endocrine hormone-producing cells.

BACKGROUND

The pancreas is composed of two distinctly different tissues. The bulk of the pancreas consists of exocrine tissue that produces a fluid that facilitates the digestion of proteins, fats, and carbohydrates. Located in discrete clusters throughout the exocrine tissue are aggregates of endocrine cells that produce the several different hormones, notably including insulin and glucagon. These aggregates, termed Islets of Langerhans, are composed of several different cell types. Among these are alpha cells that secrete glucagon; beta cells that secrete insulin; gamma cells that produce pancreatic polypeptide (PP); and delta cells that secrete somatostatin.

Each of these hormones plays an important role in regulating metabolism. For example, PP is known to stimulate gastric and pancreatic exocrine secretions; somatostatin is known to regulate the secretion of other hormones such as growth hormone, insulin, and glucagon; and insulin and glucagon are known to be critical for regulating serum glucose levels. The dramatic physiological effects resulting from abnormal regulation of these hormones underscores their importance in homeostasis. A notable example of this is diabetes mellitus resulting from insufficient insulin production.

SUMMARY

Methods of making cells that produce pancreatic endocrine hormones have been developed. Transplantation of these cells into an animal subject suffering from an insufficiency of a pancreatic hormone reversed this insufficiency.

Accordingly, the invention includes cells having a pancreatic endocrine cell-like phenotype that have been made by in vitro trans-differentiation from hepatic stem cells. Such cells include those that produce insulin, proinsulin, pre-proinsulin, somatostatin, glucagon, and/or pancreatic polypeptide. Such cells can contain higher levels of mRNA encoding insulin, somatostatin, glucagon, and/or pancreatic polypeptide than do the hepatic stems cells from which they were derived.

Also within the invention is a method for making cells having a pancreatic endocrine cell-like phenotype. This method includes the steps of: (a) providing hepatic stem cells; and (b) culturing the hepatic stem cells in vitro under conditions that result in the trans-differentiation of the hepatic stem cells into cells having a pancreatic endocrine cell-like phenotype. The step (b) of culturing the hepatic stem cells can include culturing the cells in a medium having greater than 5.5 mM glucose (e.g., at least 10 mM glucose). The medium can include RPMI 1640 supplemented with fetal calf serum.

In another aspect, the invention includes a method of reducing a pancreatic endocrine hormone insufficiency in a subject. This method includes introducing into the subject a composition comprising cells having a pancreatic endocrine cell-like phenotype that have been made by in vitro trans-differentiation from hepatic stem cells in an amount effective to reduce the pancreatic endocrine hormone insufficiency in the subject. The cells having a pancreatic endocrine cell-like phenotype can be derived from hepatic stem cells obtained from the subject, or can be derived from hepatic stem cells not obtained from the subject. The cells having a pancreatic endocrine cell-like phenotype can be introduced into the subject by implantation into a target tissue or organ (e.g., liver).

The term "subject," as used herein, means a human or non-human animal, including but not limited to a mammal such as a dog, cat, horse, cow, pig, sheep, goat, chicken, primate, rat, and mouse.

As used herein, the term "trans-differentiation" refers to the conversion of one differentiated cell type to another. Trans-differentiation can include, for example, the conversion of a liver cell to a cell having a pancreatic endocrine cell-like phenotype.

By term "hepatic stem cell" is meant any stem cell (i.e., any cell with that can serve as a progenitor for another, more differentiated cell type) found in the liver of an animal at any stage of development from embryo to adult. This may include hematopoetic stems cells that reside in the liver at any stage of development of the animal.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1A:
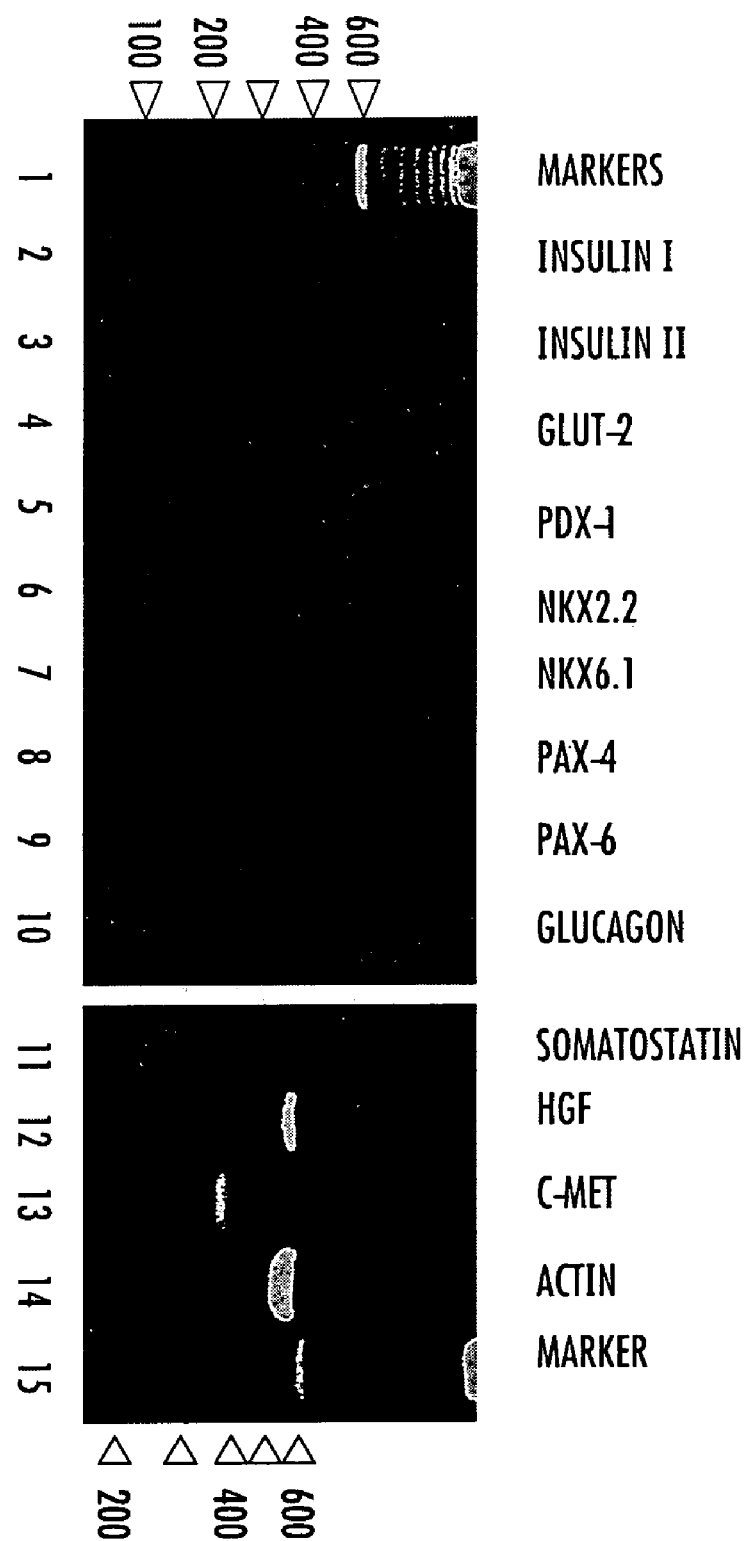
FIGS. 1A and 1B are gels showing presence of RT-PCR products related to pancreatic endocrine development by primary hepatic stem cell cultures (FIG. 1A) and trans-differentiated hepatic stem cells after long-term culture in high-glucose differentiation medium (FIG. 1B).

The invention provides methods for trans-differentiating hepatic stem cells to cells having a pancreatic endocrine cell-like phenotype. The cells made by these methods can be used to reduce a pancreatic endocrine hormone insufficiency in a subject by introducing the trans-differentiated pancreatic endocrine hormone-producing cells into the subject. In one version of the method, hepatic stem cells are placed under in vitro culture conditions (e.g., high glucose) that promote trans-differentiation of hepatic stem cells within primary cultures into cells having a pancreatic endocrine cell-like phenotype.

Hepatic stem cells cultured in vitro under such conditions form islet-like clusters interconnected with duct-like structures. The trans-differentiated cells making up these clusters express mRNA transcripts for the endocrine hormones insulin I, insulin II, glucagon, and somatostatin. When stimulated with glucose, these cells synthesize and secrete insulin, a response enhanced by nicotinamide. The cells also produce glucagon and PP, but not detectable levels of the hepatic cell marker Hep-par, as determined by immunohistochemistry. The trans-differentiated cells further express differentiation markers of endocrine pancreas, including Pdx-1, PAX-4, PAX-6, NKx2.2 and NK6.1 as well as glucose transporter-2. These cells retained the ability to produce an endocrine hormone when introduced into an animal subject. For example, transplanted islet cell-like clusters derived from the trans-differentiated cell cultures reversed hyperglycemia in an animal model of diabetes.

Biological Methods

Methods involving conventional biological, cell culture, immunological and molecular biological techniques are described herein. Such techniques are generally known in the art and are described in detail in methodology treatises. Cell culture techniques are generally known in the art and are described in detail in methodology treatises such as Culture of Animal Cells: A Manual of Basic Technique, 4th edition, by R. Ian Freshney, Wiley-Liss, Hoboken, N.J., 2000; and General Techniques of Cell Culture, by Maureen A. Harrison and Ian F. Rae, Cambridge University Press, Cambridge, UK, 1994. Immunological methods (e.g., preparation of antigen-specific antibodies, immunoprecipitation and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Molecular biological techniques are described in references such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981.

Hepatic Stem Cells

Methods of the invention utilize hepatic stem cells as source cells from which cells having a pancreatic endocrine cell-like phenotype can be made. Hepatic stem cells can be derived from the liver of any animal known to contain such stem cells, e.g., rodents such as rats, and primates such as human beings. A variety of methods for obtaining hepatic stem cells suitable for use in the invention is known. Any one of these might be might be used.

In general, hepatic stem cells may be obtained from a liver that (1) has been damaged and (2) prevented from regenerating. As described below, large numbers of hepatic stem cells were obtained from the liver of an animal that was administered a first agent that prevents hepatocyte regeneration and then a second agent (e.g., a chemical or trauma) that kills liver cells. As an example of a specific protocol, hepatic stem cell activation, proliferation, and differentiation can be induced in rats by a two-step procedure. In the first step, the animals are exposed to 2-acetylaminofluorene (2-AAF) to suppress hepatocyte proliferation. In the second step, liver injury is induced by either partial hepatectomy or by treatment with carbon tetrachloride. Petersen, et al., Hepatology 27, 1030–1038 (1998). This protocol results in the activation of resident hepatic stem cells.

Once activated, hepatic stem cells can be purified from liver based on their expression of certain cell surface markers. A number of techniques for such purification are known, e.g., antibody-based methods such as fluorescence-activated cell sorting (FACS), immunopanning, magnetic bead separation, and negative selection. Activated hepatic stem cells are known to express high levels of surface Thy-1, cytokeratin (CK)-19, OC.2 and OV6, as well as cytoplasmic alpha-fetoprotein (AFP) and gamma-glutamyl-transpeptidase (GGT) (Dabeva, et al. Proc. Natl. Acad. Sci. U.S.A. 94:7356–7361, 1997; Lemire et al., Am. J. Pathol. 139: 535–552, 1991; Petersen, et al., Hepatology 27: 433–445, 1998; Shiojiri et al., Cancer Res. 51: 2611–2620, 1991.) Using such markers, FACS can be employed to purify hepatic stems cells to a purity approaching 97%.

Because one aspect the invention relates to transplantation into humans, a preferred source of mammalian hepatic stem cells is human liver. Hepatic stem (or stem-like) cells from humans can be obtained, for example, by core biopsy of the liver. Following dispersion of the liver cells using enzymes such as trypsin and collagenase, primary cultures can be established as described below. Upon prolonged culturing, the vast majority of the cells die, leaving only the proliferating stem cells that can be clonally expanded. Other methods for obtaining human hepatic stem (or stem-like) cells are described in, e.g., published U.S. patent applications 20020182188 to Reid et al. and 20010024824 to Moss et al.

Primary Culture of Hepatic Stem Cells

Although hepatic stem cells might be trans-differentiated immediately after harvesting from a liver, it is often desirable to establish an in vitro culture of hepatic stem cells for use at a convenient time. Because stem cells have a tendency to differentiate in in vitro cultures, culture conditions should be selected to prevent such differentiation. Methods of maintaining hepatic stem cells in in vitro cultures are known.

In general, such techniques involve culturing such cells in a medium containing various stem cell growth factors. An exemplary medium a base medium (e.g., IMDM, RPMI 1640, DMEM), serum (e.g., fetal calf serum) or a serum substitute (to avoid the possibility to viral or prion contamination), stem cell growth factors, and antibiotics and/or other additives conventionally added to tissue culture media.

Although a number of commercially available base media might be used in the invention, those previously shown to support stem cell cultures are preferred. For example, Iscove's Modified Dulbecco's Medium (IMDM; Invitrogen Life Technologies, Carlsbad, Calif., Cat. #21056-023) is preferred for use in the invention. Antimicrobials such as antibiotics (e.g., gentamycin [Invitrogen Life Technologies, Carlsbad, Calif., Cat. #15750-060] or penicillin/streptomycin), antifungal compounds, and/or antiviral compounds can be added to the base medium to prevent contamination of the cultures. Insulin (Sigma, St. Louis, Mo., Cat. #I-5500) can optionally be added to the medium to support the growth of stem cells.

Preferred concentrations by volume of each of the foregoing are in the following ranges: base medium, about 60–90% (e.g., 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91%); gentamicin, about 0.05–0.2% (e.g., 0.04, 0.05, 0.06, 0.07, 0.08, 0.09, 0.1, 0.2, 0.3%); insulin, about 0.5–2.0% (e.g., 0.4, 0.5, 0.6, 0.7, 0.8, 0.9, 1, 1.5, 2, 2.5%); and serum or serum substitute, about 5–30% (e.g., 4, 5, 6, 7, 8, 9, 10, 11, 12, 13, 14, 15, 16, 17, 18, 19, 20, 21, 22, 23, 24, 25, 26, 27, 28, 29, 30, 31%).

Examples of growth factors that, when added to a medium, facilitate culturing of hepatic stem cells include leukemia inhibitory factor (LIF), stem cell factor (SCF), interleukin-3 (IL-3), and Flt-3 ligand. Such growth factors may be used at concentrations in the following ranges: LIF, about 0.1–100 ng/ml (e.g., 0.05, 0.1, 0.5, 1, 2, 5, 10, 25, 50, 75, 85, 95, 100 ng/ml); SCF, about 0.1–100 ng/ml (e.g., 0.05, 0.1, 0.5, 1, 2, 5, 10, 25, 50, 75, 85, 95, 100 ng/ml); IL-3, about 0.1–100 ng/ml (e.g., 0.05, 0.1, 0.5, 1, 2, 5, 10, 25, 50, 75, 85, 95, 100 ng/ml); and Flt-3 ligand, about 0.1–100 ng/ml (e.g., 0.05, 0.1, 0.5, 1, 2, 5, 10, 25, 50, 75, 85, 95, 100 ng/ml). In one example, these growth factors are added to the media in the following concentrations: 10 ng/ml LIF, 10 ng/ml SCF, 10 ng/ml IL-3, and 10 ng/ml Flt-3 ligand.

As a specific example, for propagation of human hepatic stem (or stem-like) cells, freshly prepared liver cell suspension is plated in 6-well plates (e.g., at a density of $3\times10^5$ cells within 3 ml of medium) or T-25 flasks (e.g., at a density of $5\times10^6$ cells into T-25 flasks in 6 ml of medium) in RPMI 1640 medium (Invitrogen Rockville, Md. cat# 11875-085, containing 5.5 mM glucose) plus fetal bovine serum (Hyclone, Logan Utah cat# SH30118.03) at 20%, with the following additives: 100 U penicillin (Invitrogen, Rockville, Md. cat#15240-062), 1000 U streptomycin (Invitrogen, Rockville, Md. cat#11860-038), and IX insulin transferrin selenium (Invitrogen, Rockville, Md. cat# 41400-045). This medium is termed Medium A. The cells are then cultured for 48 hours at 37° C. in a humidified 5% $CO_2$ incubator. The culture supernatant (containing non-adherent cells) is removed from the plate or flask, and the remaining adherent cells are washed twice with phosphate-buffered saline (PBS). Fresh Medium A (6 ml for T-25 flask, 12 ml for T-75 flask and 3 ml each well for 6-well plates) is added to the plate or flask, and the cells are cultured under the above conditions for an additional two to three weeks until spindle-shaped adherent cells in the cultures reach 70–80% confluence. The cells are then removed from the surface of the plate or flask by first washing the cells twice with PBS and then using trypsin-EDTA (Sigma) to release cells into medium containing 10% fetal bovine serum (FBS). The cells are centrifuged down, washed twice with the same medium, then resuspended at $1\times10^5$ or $1\times10^6$ cells per ml in Medium A, and re-plated in Medium A at a 1:3 dilution (one flask is passaged into three flasks of the same size). After four passages, the stem cells become a homogeneous population with spindle morphology.

Culture Conditions for Trans-differentiation of Hepatic Stem Cells into Cells that Produce at Least One Pancreatic Endocrine Hormone The method for making cells having a pancreatic endocrine cell-like phenotype includes a step of culturing the hepatic stem cells under conditions that result in the trans-differentiation of the hepatic stem cells into cells having a pancreatic endocrine cell-like phenotype. One version of this method involves culturing hepatic stem cells in a differentiation medium (DM) having greater than 5.5 mM glucose (e.g., 6, 7, 8, 9, 10, 11, 12, 13, 14, 15, 16, 17, 18, 19, 20, 21, 22, 23, 24, 25, 26, 27, 27, 28, 29, 30 mM). A number of different media containing greater than 5.5 mM glucose suitable may be used as the DM. Each generally includes a base medium (e.g., IMDM, RPMI 1640, DMEM), fetal bovine serum, added glucose and, optionally, an antibiotic and/or other additives conventionally added to tissue culture media.

DM base medium (e.g., IMDM, RPMI 1640, DMEM) can be supplemented with fetal bovine serum in a range from about 5%–25% (e.g., 5, 10, 15, 20, 25, 30%). Additional glucose in the DM can yield a final concentration of glucose greater than 5.5 mM glucose. A preferred range of glucose concentration is 10–50 mM (e.g., 10, 13, 16, 19, 21, 24, 27, 30, 33, 36, 39, 42, 45, 48, 50 mM). Although, in some cases, glucose concentrations lower than 10 mM were able to cause the trans-differentiation of hepatic stem cells into cells with a pancreatic endocrine cell-like phenotype, to expedite the trans-differentiation process glucose concentrations of 10 mM or more are preferred. An exemplary high-glucose DM is RPMI 1640 medium supplemented with 10% fetal calf serum (FCS) and about 17.5 mM glucose, to yield a final glucose concentration of about 23 mM (i.e., between 20 and 25 mM). As described in examples below, this medium was found to be advantageous for induction of a large number of pancreas-specific transcripts in long-term primary cultures of hepatic stem cells previously maintained in a serum-free Iscove's modified Dulbecco's medium. Whether a particular DM is effective in trans-differentiating a particular population of hepatic stem cells to cells with a pancreatic endocrine cell-like phenotype can be determined empirically according to the methods described in the Examples section, e.g., the hepatic stem cells are cultured in the particular DM being tested, and the cells in the culture are observed for morphological changes consistent with trans-differentiation (e.g., cluster formation) or for expression of pancreatic endocrine hormones or mRNA encoding such hormones.

DM may be supplemented with growth factors to promote expansion of differentiated hepatic stem cells. Many growth factors are known, and any factor suitable for promoting expansion of differentiated hepatic stem cells can be used. Several growth factors, e.g., basic fibroblast growth factor (bFGF), epidermal growth factor (EGF), and hepatocyte growth factor (HGF) may be especially suitable, having previously been shown to promote development of beta cells of the pancreas (Hellerstrom C and Swenne I, Diabetes 40

Suppl 2:89–93.) Such growth factors may be used at concentrations in the following ranges: bFGF, about 0.01–10 ng/ml (e.g., 0.005, 0.01, 0.03, 0.05, 0.1, 0.5, 1, 3, 5, 7, 10 ng/ml); EGF, about 0.1–100 ng/ml (e.g., 0.05, 0.1, 0.5, 1, 2, 5, 10, 25, 50, 75, 85, 95, 100 ng/ml); HGF, about 50–500 ng/ml (e.g., 50, 100, 150, 200, 250, 300, 350, 400, 450, 500 ng/ml). In one example of DM, these growth factors are added to RPMI 1640 medium containing about 23 mM glucose and 10% FBS in the following concentrations: FGF, 1 ng/ml, EGF, 10 ng/ml, and HGF 100 ng/ml.

DM may also be supplemented with factors to further promote expression and functional capabilities of a beta cell phenotype. Any factor known to promote beta cell maturation can be used. Preferred factors of this type include nicotinamide, betacellulin, insulin, selenium and transferrin. A convenient mixture of insulin, selenium and transferrin is ITS PREMIX (Becton Dickinson), containing the three factors each at a final concentration of 5 μg/ml. These components may be used at concentrations in the following ranges: nicotinamide, about 1–30 mM (e.g., 1, 3, 5, 7, 9, 11, 13, 15, 17, 19, 21, 23, 25, 27, 30); betacellulin, about 0.1–10 nM (e.g., 0.05, 0.1, 0.5, 1, 2, 3, 4, 5, 6, 7, 8, 9, 10 mM); ITS PREMIX (Gibco, catalog # 41400-045), at about 1:50–1:150 dilution (e.g., 1:40, 1:50, 1:60, 1:70, 1:80, 1:90, 1:100, 1:110, 1:120, 1:130, 1:140, 1:150, 1:160 dilution). In one example, nicotinamide (10 mM) is added to DM based on RPMI 1640 with 23 mM glucose and 10% FBS. The latter step has been found to cause enhanced expression of pancreas-related transcripts, especially insulin, in cells cultured under high glucose conditions.

In another composition, the above factors (i.e., nicotinamide (10 mM), betacellulin (2 nM), and ITS PREMIX) can be used following differentiation and expansion of pancreatic precursor cells, to further promote beta cell maturation. Once cells have progressed to the maturation stage, high glucose may be no longer necessary, and it may be desirable to switch to low-glucose, low-serum medium (e.g., RPMI 1640, glucose concentration 5.5 mM) in the presence of serum concentrations ranging from about 1–8% (e.g., 1, 2, 3, 4, 5, 6, 7, 8%), with nicotinamide, betacellulin and ITS added in the indicated concentrations. In a preferred composition for maturation of pancreatic endocrine hormone-producing cells, the components are as follows: RPMI 1640 medium, 5% FBS, nicotinamide (Sigma, 10 mM), betacellulin (2 nM) and ITS, 5 μg/ml.

In general, to induce differentiation of the hepatic stem cells into which cells having a pancreatic endocrine cell-like phenotype, the primary hepatic stem cell cultures prepared as described above are switched to high-glucose DM as described above. Cells are cultured in this medium at 37° C. in a humidified 5% $CO_2$ incubator. The medium is replaced with fresh twice every week, and the cultures are split into new containers containing fresh DM after the cells reach confluency. The cells can be cultured in this manner for 30 or more generations or passages, during which time the cells are monitored for phenotypic changes and expression of pancreatic endocrine cell markers such as insulin. Phenotypic changes that signal trans-differentiation include establishment of islet-like clusters within the cultures connected by duct-like structures. After detection of insulin gene expression, if desired, the cells may be switched to a maturation-promoting medium as described above, containing a low glucose concentration (e.g., RPMI 1640; 5.5 mM glucose), low serum (e.g., 5% FBS), nicotinamide (10 mM, Sigma), and ITS PREMIX. Cells may be cultured in maturation medium for about 2–4 weeks to promote β cell maturation and to increase sensitivity of the cells to glucose stimulation. Additional protocols for promoting β cell maturation are known in the art and may be used in the invention. For example, to modulate cell maturation, other β cell maturation factors such as arginine-glucose, glucagon, tolbutamide-glucose, and theophylline-glucose can be added to the maturation medium. See Hellerstrom et al., Diabetes Supp. 2:89–93, 1991; and Buschard et al., Int. J. Exp. Diabetes Res. 1:1–8, 2000.

Detection of Pancreatic Endocrine Hormones

To determine whether hepatic stem cells are successfully trans-differentiated into pancreatic endocrine-like cells, the cells can be examined for expression of one or more pancreatic endocrine hormones, e.g., insulin (or precursors thereof such as proinsulin and preproinsulin), glucagon, pancreatic polypeptide (PP), and somatostatin. Hormone expression can be analyzed by any known technique. For example, antibody-based assays such as immunoprecipitation and Western blotting with anti-insulin antibodies can be used to evaluate insulin release by islet-like clusters derived from hepatic stem cells. To evaluate the functionality of in vitro-generated insulin-producing islet cells, enzyme-linked immunosorbent assay (ELISA) or radioimmunoassay (RIA) can be used to measure insulin release upon glucose stimulation. In one such approach, measurements of insulin secretion by isolated islets or islet-like insulin-secreting clusters are monitored using an on-line competitive immunoassay based on capillary electrophoresis to monitor insulin secretion (Tao L et al., Electrophoresis 19:403–408, 1998). Functional studies in real time can also be undertaken utilizing measurements such as influx of extracellular $Ca^{2+}$ (Valdeolmillos M et al., J Physiol 455:173–186, 1992; Martin F et al., Diabetes 44:300–305, 1995) or release of zinc (Gee K, J Am Chem Soc 124:776–779, 2002), both of which are correlated with insulin exocytosis and extracellular release by beta cells in isolated pancreatic islets.

Earlier stages in the progression of hepatic stem cells to pancreatic endocrine hormone-producing cells can be monitored by any of the standard techniques available to test for expression of mRNA and protein of pancreas-specific markers (e.g., insulin I, insulin II, glucagon, PP, somatostatin, Pdx-1, PAX-4, PAX-6, NKx2.2, NK6.1, and glucose transporter-2). Analysis of expression of such markers by islet-like clusters appearing in hepatic hepatic stem cell cultures is helpful in determining the state of differentiation of the cells, and their potential to develop into hormone-secreting cells. Such information is useful in determining optimal culture conditions for stem cell differentiation, and in directing efforts toward propagation of the most appropriately differentiated clusters.

Expression of pancreas-specific markers can be analyzed by any suitable technique known for analyzing expression of such genes. For example, marker expression can be determined directly by assessing protein expression of cells or fluid, such as tissue culture medium. Protein expression can be detected, e.g., using antibodies that specifically bind the protein (e.g., insulin I, insulin II, glucagon, PP, somatostatin, Pdx-1, PAX-4, PAX-6, NKx2.2, NK6.1, and glucose transporter-2) in assays such as immunofluorescence or immunohistochemical staining and analysis, ELISA, RIA, immunoblotting (e.g., Western blotting), and like techniques. Expression of pancreas-specific markers can also be determined by directly or indirectly measuring the amount of mRNA encoding such markers in a cellular sample using known techniques such as Northern blotting and PCR-based methods such as competitive Q-RT-PCR. Suitable methods for analyzing expression of insulin I, insulin II, glucagon, PP, somatostatin, Pdx-1, PAX-4, PAX-6, NKx2.2, NK6.1, and glucose transporter-2 are described in the examples below; nonetheless, other suitable methods might also be employed.

In another aspect, the invention provides cells having a pancreatic endocrine cell-like phenotype. These cells are prepared according to the methods of the invention, described above. Islet-like clusters of the invention showing capability for appropriate secretion of endocrine hormone, e.g., secretion of insulin in response to glucose challenge, are useful for cell therapeutic procedures such as transplantation into a subject having a pancreatic endocrine hormone insufficiency.

Method of Reducing a Pancreatic Endocrine Hormone Insufficiency

In yet another aspect, the invention provides a method of reducing a pancreatic endocrine hormone insufficiency in a subject. This method may be performed by introducing into the subject a composition including cells having a pancreatic endocrine cell-like phenotype in an amount sufficient to reduce the pancreatic endocrine hormone insufficiency in the subject. The introduced cells can produce one or more pancreatic endocrine hormones, including insulin, somatostatin, glucagon, and pancreatic polypeptide.

Suitable subjects for use in the invention can be any animal. For example, the subject can be an animal such as mammal like a dog, cat, horse, cow, pig, sheep, goat, chicken, primate, rat, or mouse. Preferred are subjects suspected of having or at risk for developing a disorder of pancreatic endocrine hormone insufficiency, e.g., a person suspected of having or at risk for developing type I or type II diabetes, based on clinical findings or other diagnostic test results.

The cells/compositions of the invention can be administered to animals or humans by any conventional technique. Such administration might be parenteral (e.g., intravenous, subcutaneous, intramuscular, or intraperitoneal introduction). Preferably, the compositions may also be administered directly to the target site (e.g., to the liver, pancreas, renal subcapsular space or skin) by, for example, surgical delivery, such as implantation to an internal or external target site, or by catheter to a site accessible by a blood vessel. Implantation may include inserting implantable cellular delivery systems that permit release of secreted hormones, but prevent destruction of the hormone-secreting cells by the immune cells of the host.

A preferred method of introduction of the cells of the invention may be by techniques currently in use for transplantation of islet cells recovered from the pancreata of human cadavers. See, e.g., Shapiro A J M et al., N Engl J Med 343:230–238, 2000. In this method, islets (or cells) are delivered under local anaesthesia, by x-ray fluorographic guidance of a long thin needle, into the portal vein of the liver. Once in the portal circulation, the islet cells enter the portal spaces and take up residence, becoming surrounded by new blood vessels. The rich blood supply in the vicinity of the transplanted cells promotes effective secretion of hormones directly into the blood stream.

An effective number of pancreatic endocrine hormone-producing cells sufficient for reducing or eliminating a pancreatic hormone insufficiency can be determined by established procedures for evaluation of outcomes of pancreatic islet cell transplantation. It is contemplated that fewer stem-cell derived clusters may be required than in the case of human donor islets, given the ready availability and recoverability of viable islet-like clusters grown in vitro. For example, in studies disclosed herein, hyperglycemia in the NOD-acid rodent model was normalized in animals receiving implants containing as few as 200 islet-like clusters. In general, determination of an effective amount of the composition is made using standard methods known in the art, such as measurement of blood glucose levels in the subject before and after administration of the cells/compositions.

The source of the hepatic stem cells used to produce the pancreatic endocrine hormone-producing cells that are introduced into the subject can either be autologous or heterologous. The option of producing autologous cells from the subject presents an attractive alternative to a regimen of lifelong immunosuppressive therapy to control the risk of rejection of the introduced cells. Autologous pancreatic endocrine hormone-producing cells can be prepared, as described above, by obtaining a liver biopsy from the subject by routine procedures, and propagating the hepatic stem cells contained within the liver biopsy, to produce pancreatic endocrine hormone-producing cells.

The methods of this invention, generally speaking, may be practiced using any mode of administration that is medically acceptable, meaning any mode that produces effective levels of response without causing clinically unacceptable adverse effects.

EXAMPLES

The present invention is further illustrated by the following specific examples. The examples are provided for illustration only and are not to be construed as limiting the scope or content of the invention in any way.

Example 1

Isolation and Culture Primary Hepatic Stem Cells

Activation and isolation of hepatic stem cells. Hepatic stem cell activation was performed in rats as previously described using the 2-acetylamino-fluorene (2-AAF)/hepatic injury model (Petersen et al., Hepatology 27:1030–1038,1998). Activated stem cells were isolated from intact treated rat livers by a two-step collagenase perfusion (Seglen, J. Toxicol. Environ. Health 5:551–560, 1979). The cells were then purified by FACS to obtain a subpopulation of Thy-1.1-positive cells using a fluorescein isothiocyanate (FITC)-conjugated anti-rat Thy1.1 antibody (1 μg/million cells; PharMingen Inc. San Diego, Calif.) as previously described (Petersen et al., Hepatology 27, 433–445, 1998). This technique resulted in hepatic stem cell populations with a purity of >95%. Thy-1.1-positive cells isolated by this method express hepatic stem cell markers, including α-fetoprotein (AFP), albumin, γ-glutamyl transferase (GGT), cytokeratin 19 (CK19) and OV6.

In vitro culture of hepatic stem cells. The purified Thy-1.1-positive stem cells were established in primary cultures using serum-free medium, i.e., Iscove's modified Dulbecco's Medium (DMEM) (Gibco/BRL) containing a serum substitute supplemented with growth factors: leukemia inhibitory factor, LIF (10 ng/ml); interleukin-3, IL-3 (10 ng/ml); stem cell factor, SCF (10 ng/ml) and Flt-3 ligand (10 ng/ml). Hepatic stem cell cultures were maintained in this medium for prolonged periods of up to six months. To induce trans-differentiation, the cells were cultured in RPMI 1640 medium (Gibco/BRL) plus 10% FCS in the presence of an additional 17.5 mM glucose (to yield a final concentration of 23 mM glucose).

Example 2

Morphological Characteristics of Trans-Differentiated Hepatic Stem Cell Cultures The stem cells isolated as described in Example 1 were used to establish an in vitro culture in serum-free Iscove's modified DMEM supplemented with growth factors. This culture as maintained continuously for more than 6 months. Throughout this period, the cells maintained a stellate, stem-like phenotype and expressed AFP, Thy-1.1, c-kit, and CD34 as determined by immunohistochemistry.

To induce trans-differentiation, the cells were replated and cultured in RPMI 1640 medium supplemented with 10% FCS and 17.5 mM (23 mM final concentration) glucose. After about two months, scattered small spheroid cell clusters began to form on top of the confluent cell monolayer. Individual spheroids from these cell cultures were selected for clonal passage and were subjected several times to the high glucose (23 mM) culturing process described above. The resultant cells reached confluence, and by day 14 formed additional clusters when maintained under the high glucose conditions. After culture for a further five to seven days in the presence of 10 mM nicotinamide, the number and dimension of these spheroid cell clusters markedly increased. Multiple clusters also became connected by duct-like structures.

Example 3

PCR Characterization of Primary Hepatic Stem Cells and Trans-Differentiated Cells Reverse transcription (RT) and PCR. Total RNA was prepared from primary cultured hepatic stem cells and trans-differentiated stem cells using TRIzol (Life Technologies, Rockville, Md.). To eliminate genomic DNA contamination, mRNAs were purified using oligo-dT cellulose (MicroFastTrack 2.0 Kit, Invitrogen) according to the manufacturer's recommended protocol. The cultures were tested for transcriptional gene expression related to pancreatic organ genesis by RT-PCR or nested PCR, according to published protocols (Ramiya et al., Nat. Med. 6:278–282, 2000) with some modifications. Gene expression was analyzed for the following genes: insulin I, insulin II, glucose transporter 2 (Glut-2), PDX-1, Nkx2.2, Nkx6.1, PAX-4, PAX-6, glucagon, somatostatin, hepatocyte growth factor (HGF) and the HGF receptor, i.e., c-MET. In addition, PCR was performed without RT as a control for DNA contamination.

Oligonucleotide primers, yielding products of the sizes indicated in parentheses, were used for PCR and nested PCR amplification of the following gene transcripts: insulin I (331 bp); insulin II (209 bp);Glut-2 (304 bp); Pdx-1 (305 bp); Nkx2.2 (188 bp);Nkx6.1 (205 bp); PAX-4 (214 bp); PAX-6 (545 bp);glucagon (210 bp); somatostatin (187 bp); HGF (368 bp); c-MET (540 bp). The forward and reverse primers of each primer set were designed to be located in different exons, based on sequences obtained from GENBANK. All primers were purchased from Life Technologies.

The cDNA was synthesized from mRNA using random hexamer primers. RT-PCR and nested PCR were used for detection of all transcripts except HGF, c-MET, glucagon and actin. PCR products were obtained in all cases using 30 cycles of amplification, then separated by electrophoresis in 2.5% agarose gels. To confirm the specificity, RT-PCR products were sequenced by BIG DYE DNA sequence analysis using an ABI-377 sequencer (Applied Biosystems) according to the manufacturer's protocols.

Figure 1B:
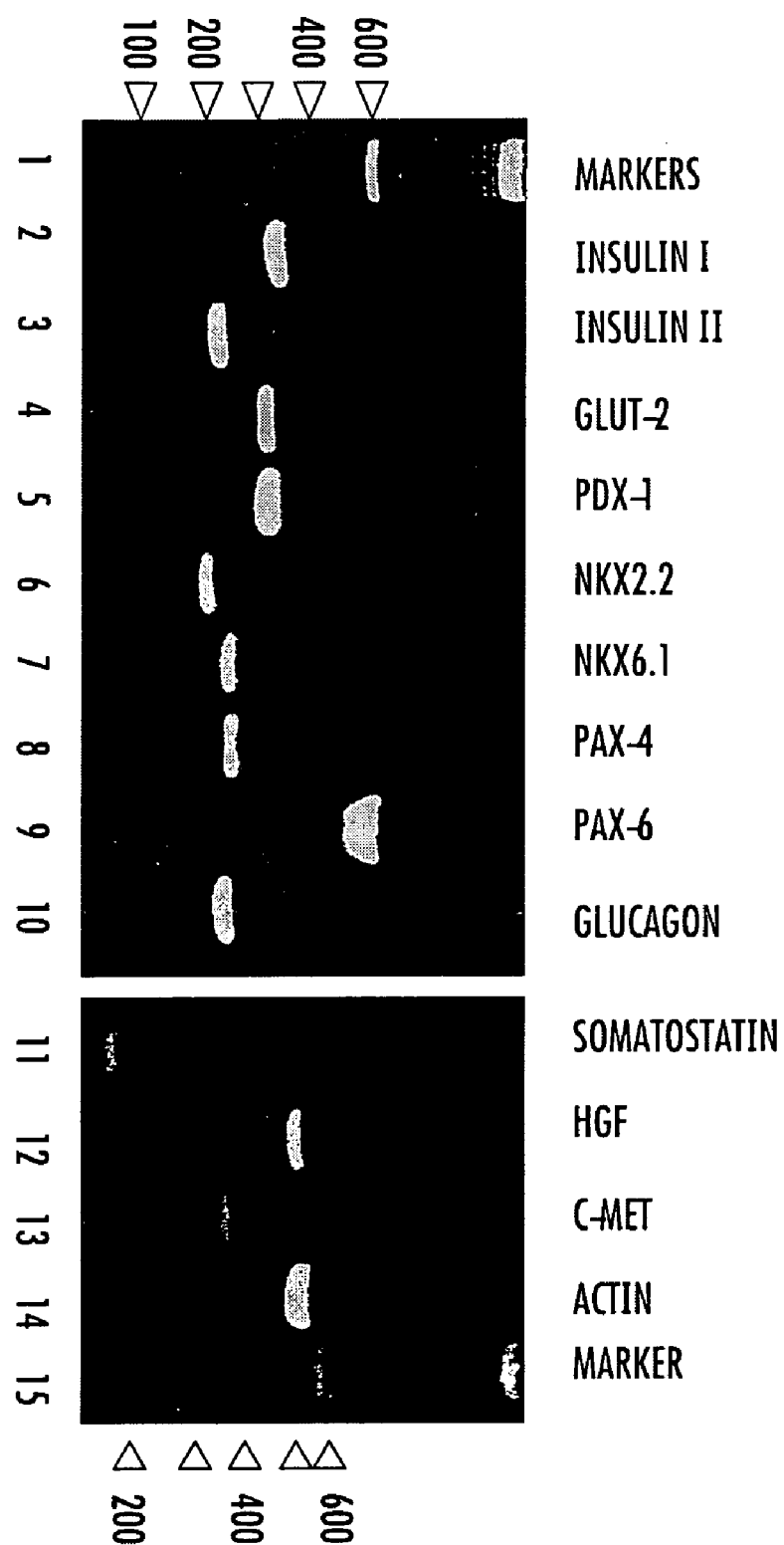

Referring to FIG. 1A, two-month primary cultures of hepatic stem cells expressed detectable levels of HGF and its receptor, c-MET. They did not, however, express differentiation markers associated with endocrine pancreas development (e.g., Pdx-1, Nkx2.2, Nkx6.1, Pax-4 and Pax-6). Nor did they express Glut-2, or any of the tested endocrine hormones (i.e., insulin I, insulin II, glucagon and somatostatin). By contrast, as seen in FIG. 1B, hepatic stem cell cultures containing islet-like clusters expressed all of the differentiation markers tested (i.e., Pdx-1, Nkx2.2, Nkx6.1, Pax-4 and Pax-6), as well insulin I, insulin II, glucagon and somatostatin, and the cell surface marker, Glut-2. In addition, these cultures continued to express HGF and c-MET.

Example 4

Immunohistochemical Characterization of Primary Hepatic Stem Cells and Trans-differentiated Cells Immunocytochemistry. Sterile microscope slide cover slips were coated with fibronectin and placed in wells of tissue culture plates. Transdifferentiated hepatic stem cells grown to confluency on the cover slips were fixed in cold acetone for ten minutes and stored at −70° C. for later assay. Immunocytochemistry was carried out using primary antibodies reactive against endocrine hormones, i.e., insulin, glucagon, and PP. All antibodies were purchased from Dako. Primary antibodies were used at following dilutions: guinea pig polyclonal to rat insulin, 1:100; rabbit polyclonal to rat glucagon, 1:75; and rabbit polyclonal to PP, 1:600. Immunoreactive signals were visualized with VECTOR BLUE using the LSAB Kit (Dako). For characterization of purified primary hepatic stem cells, freshly isolated stem cells were cytocentrifuged to slides for H&E staining and detection of hepatic stem stem cell markers as described (Petersen et al., Hepatology 27: 433–445, 1998). The trans-differentiated cells stained strongly for glucagon and PP, and diffusely for insulin. The majority of trans-differentiated cells examined stained with both anti-insulin and antiglucagon antibodies. The trans-differentiated cells did not stain for the hepatocyte protein, Hep-par. In contrast, the primary hepatic stem cells stained for Hep-par, but not for glucagon, PP, or insulin.

Example 5

Measurement of Insulin Content and Secretion

Measurement of insulin content and secretion by immunoprecipitation and Western blotting. Confluent cultures of trans-differentiated hepatic stem cells were maintained in RPMI 1640 plus 10% fetal calf serum in the presence or absence of 10 mM nicotinamide for 7 days. The cells were then switched to serum-free medium containing 0.5% BSA for 5 hrs, washed twice with serum-free medium, then stimulated with an additional 17.5 mM glucose for 2 hrs. The culture medium was collected and stored at −70° C. for assay of secreted insulin. Intracellular insulin was extracted with lysis buffer. The presence of insulin in the culture media and cell lysates was determined by immunoprecipitation with anti-rabbit-insulin polyclonal antibodies (Santa Cruz Biotechnology), followed by separation of the precipitated material by 18% SDS-PAGE, transfer to nylon membrane, and blotting with anti-insulin antibodies as described (Yang, et al., J. Biol. Chem. 269:7156–7162, 1994). Cell lysates (150 µg) or culture media (1 ml) from each culture were used for the immunoprecipitation. Normal rabbit serum was used as primary antibody control, and culture medium containing 0.5% BSA was used as a control for secreted insulin measurements. Insulin protein on the filter was visualized by chemiluminescence. Insulin content in cells and in the media was determined by pooling cell lysates and culture medium from three separate cultures.

Figure 2:
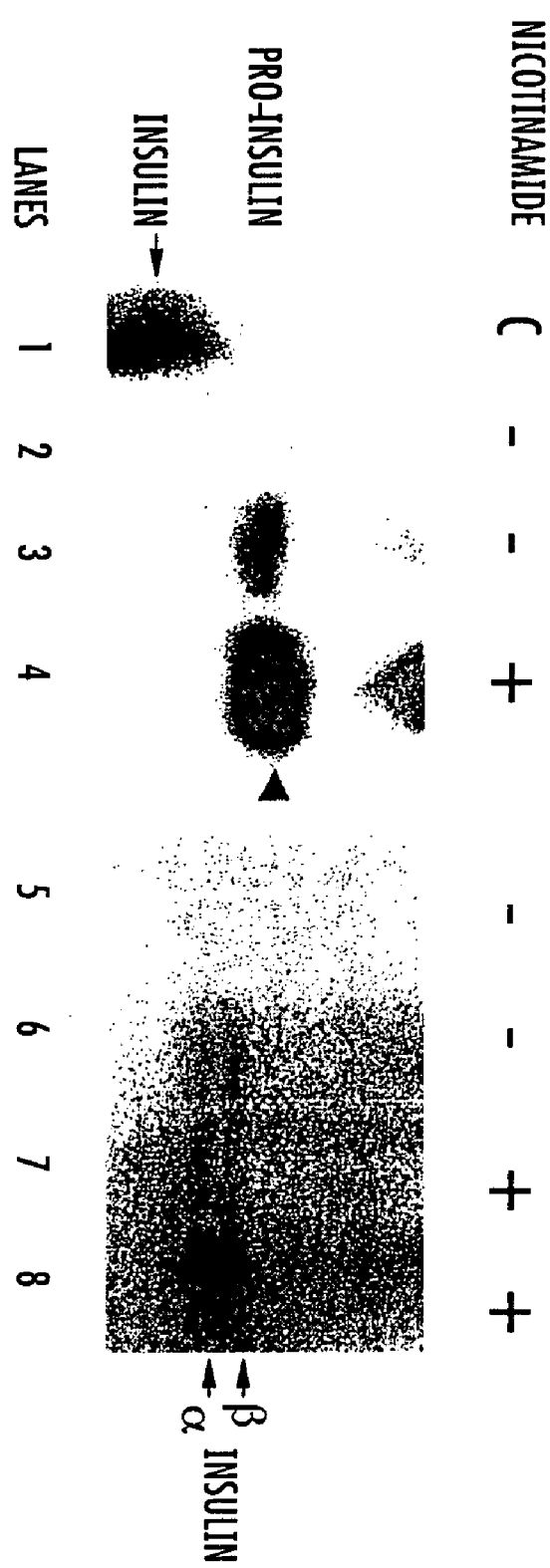
FIG. 2 is a Western blot showing cellular insulin production (left panel) and insulin secretion (right panel) by trans-differentiated hepatic stem cells. Insulin content was detected in cell lysates after 5 days of treatment with or without 10 nM nicotinamide using combined immunoprecipitation and Western blotting with anti-insulin antibodies. Lane 1, insulin control; Lanes 2 and 5, non-immune rabbit serum; Lanes 3 and 6 without nicotinamide and Lanes 4 and 8 with nicotinamide treatment. Lane 8 with glucose stimulation after nicotinamide treatment.

The results indicated that the transdifferentiated cells synthesized and stored detectable levels of insulin in response to glucose challenge and nicotinamide treatment. Referring to FIG. 2, the panel on the left shows insulin content in the cell lysates, and the panel on the right shows insulin secreted into the culture medium by these cells. In both cases, growth of the cells in nicatinamide before glucose stimulation increased the levels of insulin detected (FIG. 2, lanes 4, 7, 8). Densitometric analysis of the cell lysates indicated this increase to be 3.4 times greater than in untreated cells. Anti-insulin antibody staining on Western blots indicated that the cells stored insulin in its pro-insulin form.

Example 6

Reversal of Hyperglycemia in a Diabetic Animal

The ability of hepatic stem cell-derived islet-like cell clusters to reverse hyperglycemia was examined in vivo using streptozotocin-induced diabetic NOD-scid mice as recipients. NOD-scid mice received five intraperitoneal injections of streptozotocin (40 µg/g body weight) every other day, according to published procedures (Elliott JI et al., Clin. Exp. Immunol. 109:116–120, 1997; Gerling IC et al., Diabetes 43:433–440, 1994). Blood glucose levels were monitored daily by using an ACCU CHEK glucose detector (Roche Diagnostics). NOD-scid mice so treated were determined to have stable hyperglycemia, with blood glucose levels >350 mg/dl. Normal blood glucose levels in controls were in the range of about 70–110 mg/dl.

Four days after the fifth streptozotocin injection, one mouse was transplanted with 200 hepatic stem cell-derived insulin-producing clusters divided between the renal subcapsular space and a subcutaneous site. Two other mice received 30 such clusters, transplanted only to the subcapsular space. Three control mice received sham surgery without implants. Blood glucose levels were monitored every 2 days after-transplantation.

The mouse receiving 200 islet-like clusters exhibited normalized blood glucose levels 10 days after implantation. Control animals that did not receive implants showed persistent hyperglycemia. The two diabetic mice that received renal subcapsular transplantation of only 30 islet-like clusters continued to exhibit hyperglycemia.

Morphological characteristics and immunostaining patterns of the implanted clusters were analyzed in histological sections from the mice. Within the implant in the diabetic NOD-scid mouse with normalized blood glucose levels, increased networking of micro blood vessels was observed. Immunohistochemical staining for insulin demonstrated strong insulin staining in the cytoplasm of the implanted clusters. Results of this experiment provided evidence that the cells in these clusters further matured in the in vivo environment and functioned in response to the high blood glucose levels.

Other Embodiments

It is to be understood that while the invention has been described in conjunction with the detailed description thereof, the foregoing description is intended to illustrate and not limit the scope of the invention, which is defined by the scope of the appended claims. Other aspect s, advantages, and modifications are within the scope of the following claims.

The invention claimed is:

1. A method for making cells having a pancreatic endocrine cell phenotype, the method comprising the steps of:
   (a) isolating hepatic stem cells from the livers of 2-acetylamino-fluorene-treated adult rats; and
   (b) culturing said hepatic stem cells in vitro in a medium comprising greater than 5.5 mM glucose until said hepatic stem cells differentiate into cells having a pancreatic endocrine cell phenotype.

2. The method of claim 1, wherein the medium comprises at least 10 mM glucose.

3. The method of claim 1, wherein the medium comprises RPMI 1640 supplemented with fetal calf serum.

4. The method of claim 1, wherein the cells having a pancreatic endocrine cell phenotype produce insulin.

5. The method of claim 1, wherein the cells having a pancreatic endocrine cell-like phenotype produce somatostatin.

6. The method of claim 1, wherein the cells having a pancreatic endocrine cell-like phenotype produce glucagon.

7. The method of claim 1, wherein the cells having a pancreatic endocrine cell-like phenotype produce pancreatic polypeptide.

8. The method of claim 1, wherein the cells having a pancreatic endocrine cell phenotype contain higher levels of insulin mRNA encoding polypeptide than do the hepatic stem cells from which they were differentiated.

9. Cells having a pancreatic endocrine cell phenotype made according to the method of claim 1.

10. The cells of claim 9, wherein the cells produce insulin.

11. The cells of claim 9, wherein the cells produce somatostatin.

12. The cells of claim 9, wherein the cells produce glucagon.

13. The cells of claim 9, wherein the cells produce pancreatic polypeptide.

14. The cells of claim 9, wherein the cells contain higher levels of mRNA encoding insulin polypeptide than do the hepatic stem cells from which they were differentiated.

* * * * *